(12) United States Patent
McSpadden et al.

(10) Patent No.: US 6,419,488 B1
(45) Date of Patent: Jul. 16, 2002

(54) ENDODONTIC INSTRUMENT HAVING A CHISEL TIP

(75) Inventors: John T. McSpadden, Chattanoga, TN (US); Tim L. Taylor, Corona Del Mar, CA (US)

(73) Assignee: Ormco Corporation, Orange, CA (US)

( * ) Notice: Subject to any disclaimer, the term of this patent is extended or adjusted under 35 U.S.C. 154(b) by 0 days.

(21) Appl. No.: 08/636,608

(22) Filed: Apr. 24, 1996

Related U.S. Application Data

(63) Continuation-in-part of application No. 08/570,283, filed on Dec. 11, 1995.

(51) Int. Cl.⁷ .................................................. A61C 1/02
(52) U.S. Cl. ........................................................ 433/102
(58) Field of Search .................................. 433/102, 224, 433/165, 166

(56) References Cited

U.S. PATENT DOCUMENTS

| | | |
|---|---|---|
| 1,022,838 A | 4/1912 | Funk |
| 1,067,015 A | 7/1913 | Fowler |
| 1,211,537 A | 1/1917 | Burton |
| 1,307,446 A | 6/1919 | Kerr |
| 2,035,298 A | 3/1936 | Caldwell |
| 2,084,737 A | 6/1937 | Reamer |
| 2,328,629 A | 9/1943 | Eich et al. |
| 2,769,355 A | 11/1956 | Crisp |
| 2,966,081 A | 12/1960 | Kallio |
| 3,443,459 A | 5/1969 | Mackey et al. |
| 3,947,143 A | 3/1976 | Gulla |
| 3,971,135 A | 7/1976 | Leu |
| 3,991,454 A | 11/1976 | Wale |
| 4,190,386 A | 2/1980 | Brabetz et al. |
| 4,209,275 A | 6/1980 | Kim |
| 4,330,229 A | 5/1982 | Croydon |
| 4,332,561 A | 6/1982 | McSpadden |
| 4,457,710 A | 7/1984 | McSpadden |
| 4,536,159 A | 8/1985 | Roane |
| 4,538,989 A | 9/1985 | Apairo et al. |
| 4,602,900 A | 7/1986 | Arpaio et al. |
| 4,661,061 A | 4/1987 | Martin |
| 4,758,156 A | 7/1988 | Johnson |
| 4,894,011 A | 1/1990 | Johnson |
| 4,904,185 A | 2/1990 | McSpadden |
| 4,913,603 A | 4/1990 | Friedli et al. |
| 4,934,934 A | 6/1990 | Arpaio et al. |
| 5,035,617 A | 7/1991 | McSpadden |
| 5,035,618 A | 7/1991 | Katz et al. |
| 5,088,863 A | 2/1992 | Imanaga et al. |
| 5,104,316 A | 4/1992 | McSpadden |
| 5,106,298 A | 4/1992 | Heath et al. |
| 5,219,284 A | 6/1993 | Velvart et al. |
| 5,380,200 A | 1/1995 | Heath et al. |
| 5,387,059 A | 2/1995 | Borzemsky |
| 5,429,504 A * | 7/1995 | Peltier et al. ................ 433/165 |
| 5,464,362 A | 11/1995 | Heath et al. |
| 5,569,035 A * | 10/1996 | Balfour et al. ............... 433/165 |

FOREIGN PATENT DOCUMENTS

| | | |
|---|---|---|
| DE | 279144 | 10/1913 |
| DE | 949002 | 3/1956 |
| EP | 0195838 | 12/1989 |
| FR | 775073 | 6/1934 |
| GB | 1419624 | 12/1975 |
| GB | 2035806 | 12/1977 |
| SU | 622588 | 5/1978 |
| SU | 715238 | 2/1980 |

* cited by examiner

*Primary Examiner*—Nicholas D. Lucchesi
(74) *Attorney, Agent, or Firm*—Wood, Herron & Evans, L.L.P.

(57) ABSTRACT

An endodontic instrument for use in performing root canal procedures comprises an elongate working portion and a chisel tip portion which has removing edges that improve the effectiveness of the instrument in extirpating and enlarging the root canal.

1 Claim, 17 Drawing Sheets

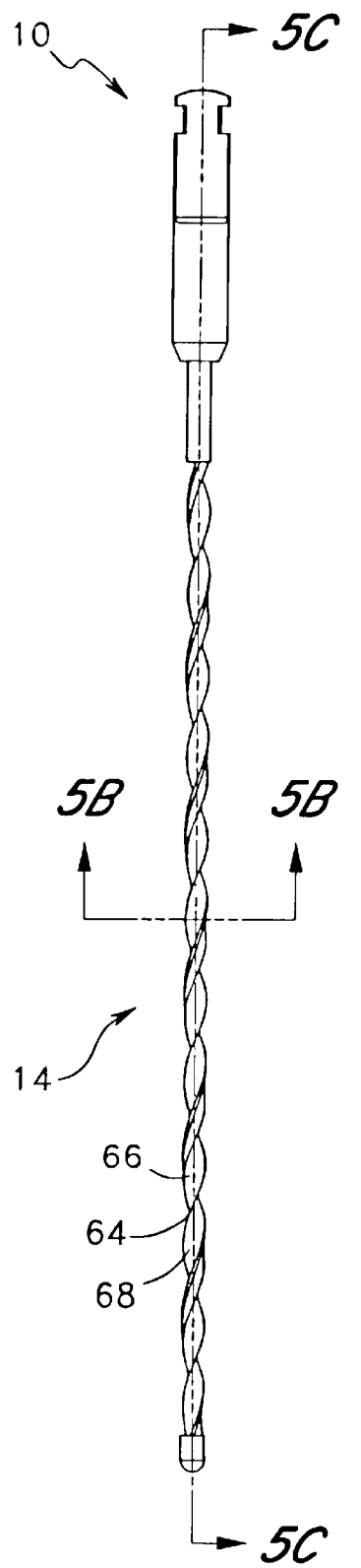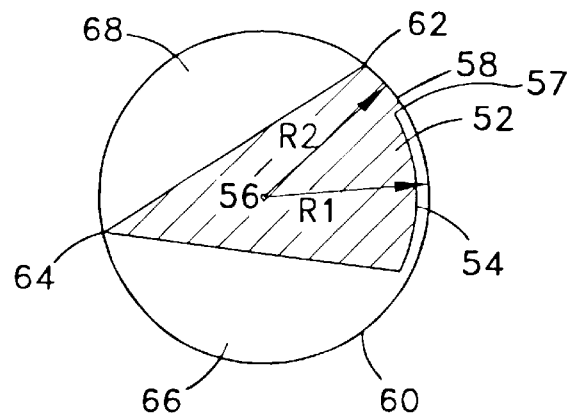
FIG. 5A    FIG. 5B    FIG. 5C

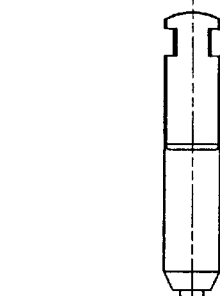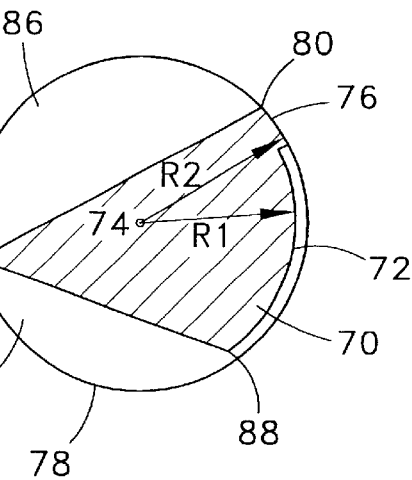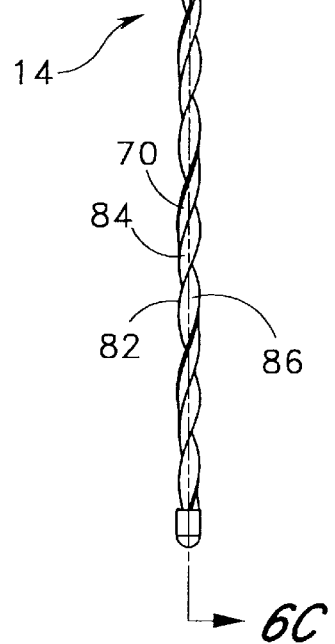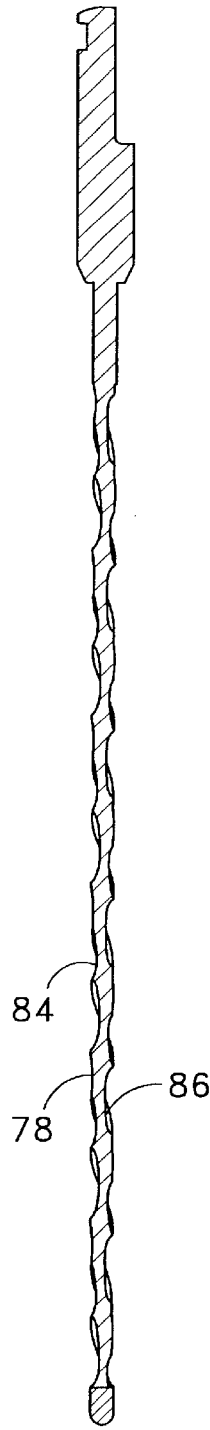
FIG.6A  FIG.6B  FIG.6C

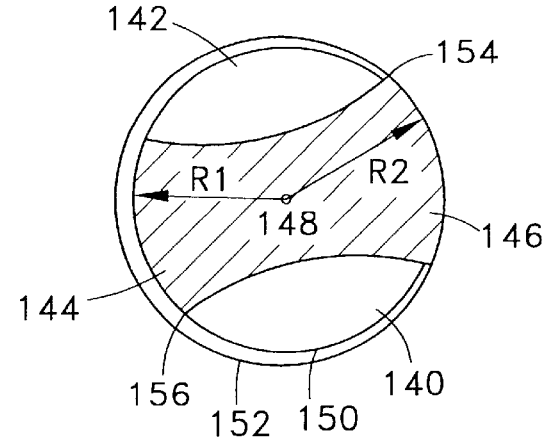
FIG.9B
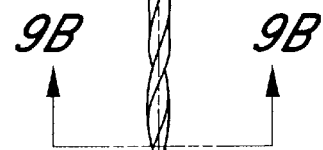
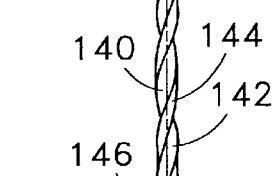
FIG.9A
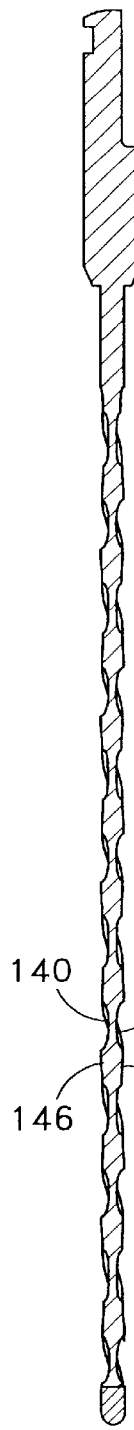
FIG.9C

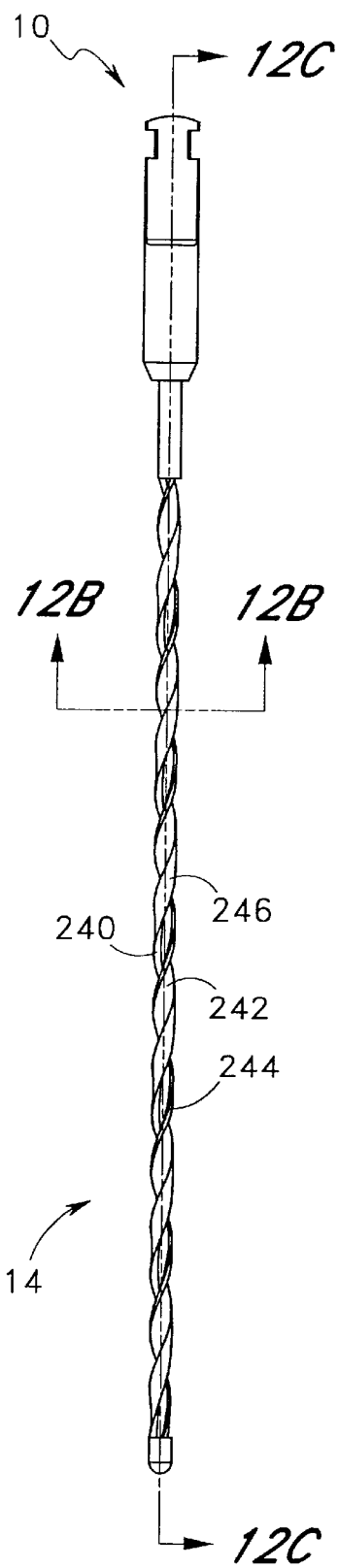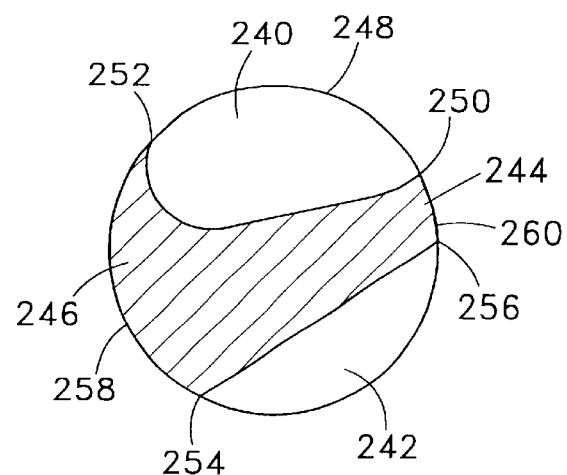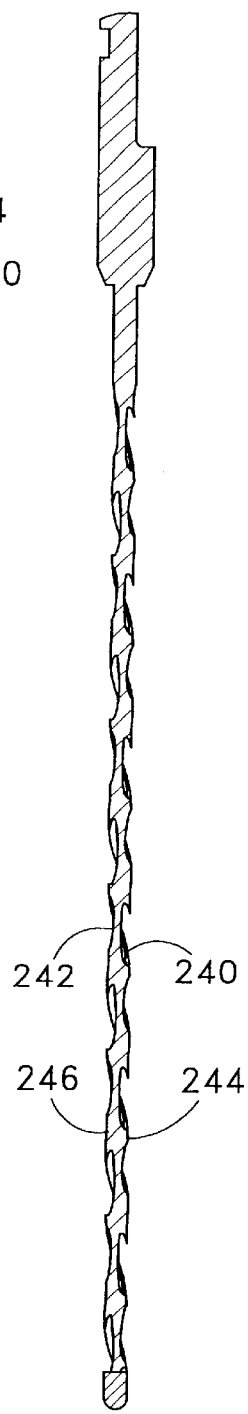
FIG. 12A
FIG. 12B
FIG. 12C

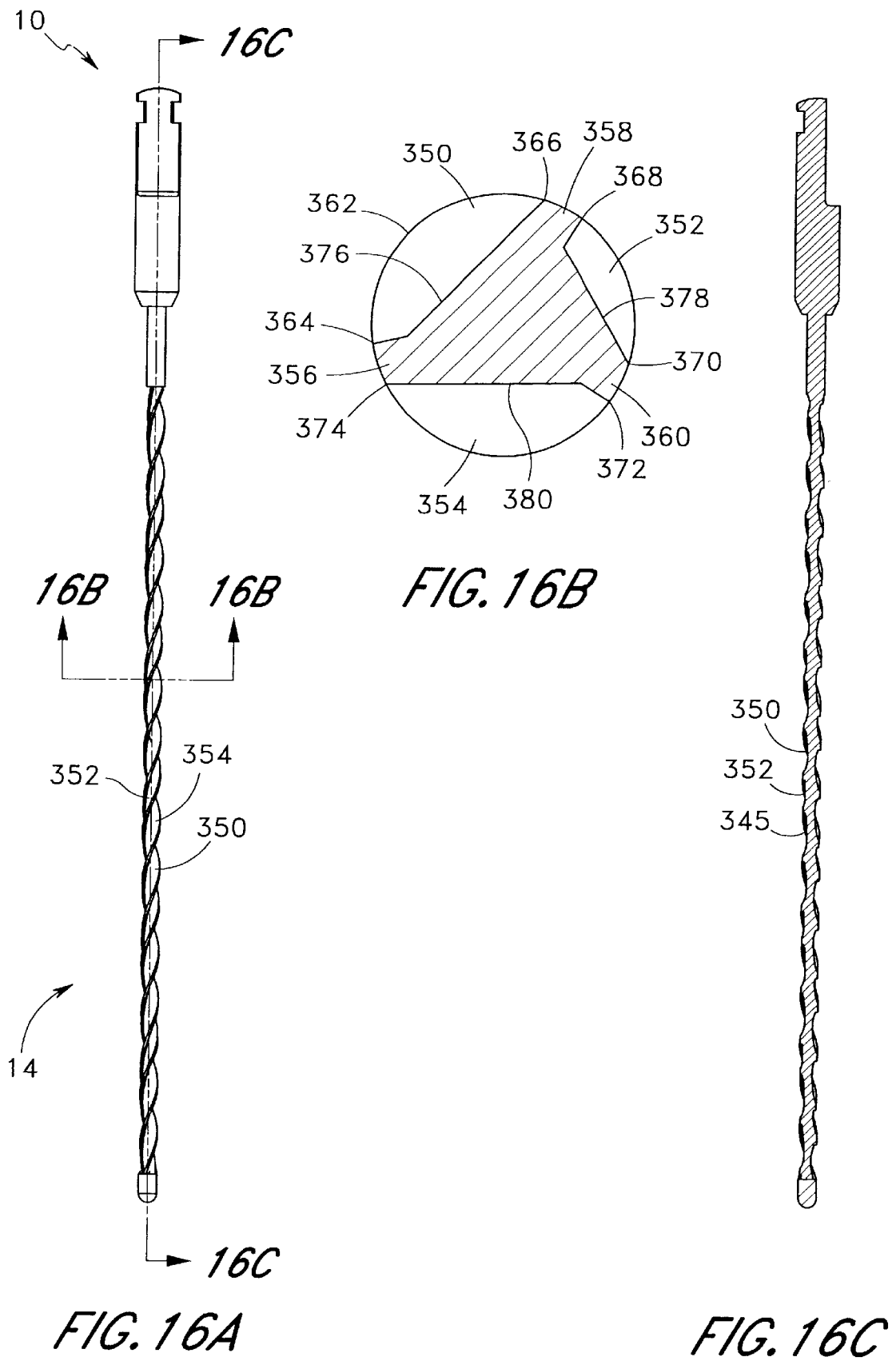

ENDODONTIC INSTRUMENT HAVING A CHISEL TIP

RELATED APPLICATIONS

This application is a continuation-in-part of co-pending U.S. patent application Ser. No. 08/570,283, filed Dec. 11, 1995, incorporated herein by reference as though fully reproduced herein.

FIELD OF THE INVENTION

This invention relates generally to the field of endodontic instruments and more particularly to reamers or files used in performing root canal procedures. The reamers are used to remove diseased tissue from the canal prior to sealing and filling the canal cavity with a suitable filler material, such as gutta-percha.

BACKGROUND

One of the more technically difficult and delicate procedures in the field of dentistry is root canal therapy. The root canal of a tooth houses the circulatory and neural systems of the tooth. These enter the tooth at the terminus of each of its roots and extend through a narrow, tapered canal system to a pulp chamber adjacent the crown portion of the tooth. If this pulp tissue becomes diseased or injured, it can cause severe pain and trauma to the tooth, sometimes necessitating extraction of the tooth. Root canal therapy involves removing the diseased tissue from the canal and sealing the canal system in its entirety. If successful, root canal therapy can effectively alleviate the pain and trauma associated with the tooth so that it need not be extracted.

To perform a root canal procedure, the endodontist first drills into the tooth to locate the root canal and then uses instruments of small diameter such as reamers and files to remove the decayed, injured or dead tissue from the canal. These are tapered instruments used to remove the diseased tissue in the root canal by reciprocating and/or rotating motion. The primary goal is to remove all of the decayed or injured nerve while leaving the integrity of the root canal walls relatively unaffected. Preserving the integrity of the root canal is important in order to allow proper filling of the root canal void in a homogenous three dimensional manner such that leakage or communication between the root canal system and the surrounding and supporting tissues of the tooth is prevented. Once as much of the diseased material as practicable is removed from the root canal, the canal is then sealed closed, typically by reciprocating and/or rotating a condenser instrument in the canal to urge a sealing material such as gutta-percha into the canal.

Since root canals are not necessarily straight and are often convoluted, it is often difficult to clean the canal while preserving its natural shape. Many instruments have a tendency to want to straighten out the canal or proceed straight into the root canal wall, altering the natural shape of the canal and sometimes transporting completely through the canal wall. Also, the opening of many root canals are small, particularly in older patients, due to calcified deposits on the root canal inner walls. Thus the files or reamers must be able to withstand the torsional load necessary to penetrate and enlarge the canal for purposes of treatment without breaking the instrument. A similar requirement exists for compactors or condensers used to fill the root canal with gutta percha. Gutta-percha used as a sealing material has a high viscosity and thermoplastic character. It is desirable, therefore, to use a condenser instrument that is able to withstand the torsional load necessary to urge the material into the canal without breaking the instrument while at the same time condensing the sealing material without leaving any voids in the canal which may lead to treatment failure.

One of the problems with traditional endodontic instruments used for extirpating and filling a root canal is that the torsional limitations of the instrument are often exceeded resulting in breakage of the instrument. Breakage of the instrument may occur as a result of the inadequate removal of dental chips which are cut from the wall of the root canal. The dental chips may be engaged between the instrument and the root canal wall resulting in friction which may cause excessive torque and thus breakage of the instrument.

Traditional reamers or files contain helical flutes along the working portion which are substantially semicircular in cross-section, that is, an arc tracing a line transverse to the flute length along the bottom of the flute wall is of substantially uniform radii at all points along the line. This structure is intended to promote advancement of tooth chips and debris up the expanding diameter of the instrument along the spiraling flute away from the tip. However, during the extirpating procedure, the dental chips which are formed may be inadequately removed from the root canal and may be forced into flutes along the instrument between the instrument and the root canal causing damage to the canal walls and/or inadequate or uneven tissue removal. This build up of debris may also lead to increased friction resistance already imposed by contact between the instrument and the canal, which in turn increases the torsional load on the instrument. In many cases, the torsional loads on the instrument exceed the tensile strength of the working portion of the instrument resulting in fracture.

Another problem that can occur is transportation or penetration through the canal wall. This can occur when a straight file or reamer is used to prepare a curved canal. The file often will want to maintain a straight path into the root canal wall instead of following the natural path of the canal. In some extreme cases, the file can actually perforate the wall of the root canal causing injuring of the supporting tissues of the tooth. One attempt to solve this problem is to provide a dental file having a smooth-walled non-cutting pilot tip for guiding the file or reamer into the curved root canal. See, for instance, U.S. Pat. No. 4,299,571 to McSpadden, incorporated herein by reference. While the provision of such a smooth-walled pilot tip represented a significant improvement in the art at the time, the design has significant drawbacks in certain cases.

The primary drawback is that the pilot tip, being blunt and smooth, has little or no cutting ability. While the blunt tip can fairly easily wedge its way into the soft, fleshy nerve, there is often difficulty encountered in a calcified root canal which has layers of calcified accretion built up along the inner wall of the canal. It is often difficult in these highly calcified root canals to penetrate through the calcified material to a depth sufficient to allow cutting to begin. When using such files having a blunt tip, the file must essentially burnish or grind its way into the calcified material before entering the canal. This generates significant heat and friction as the tip attempts to burnish its way through the hard calcified material. This can cause pain and heating of the tooth which is undesirable. It can also cause increased torsional loads on the file or reamer which can increase the risk of breakage in the canal and decreases the life of the tool.

SUMMARY OF THE INVENTION

The present invention is directed to an improved endodontic instrument for use in an endodontic root canal procedure which comprises an elongate working portion having a length of from about 3 to about 18 millimeters, a peripheral diameter ranging from about 0.08 millimeters to about 1.9 millimeters, at least one helical flute, at least one helical land and at least one tissue removing edge. Each flute and land has a pitch ranging from about 1 spiral per 16 millimeters to about 1 spiral per millimeter.

In accordance with one preferred embodiment, the above-described working portion has a chisel tip portion at the end of the working portion. The chisel tip portion comprises plural facets which intersect along a substantially linear chisel edge that is substantially orthogonal to a longitudinal axis of the elongate working portion.

In another preferred embodiment, the chisel tip portion comprises plural facets which intersect along a substantially linear chisel edge such that upon rotation of the tip portion in the root canal, each of the facets removes tissue along respective removing edges that are substantially collinear with each other along the chisel edge.

A further aspect involves a chisel tip portion at the end of the previously described working portion. The chisel tip portion comprises plural facets which intersect along a chisel edge. The facets intersect the working portion at respective tissue removing edges disposed at the periphery of the working portion. The tissue removing edges are unequally spaced about the periphery. Preferably, the flute is in working cooperation and adjacent to the land so as to provide a tissue-removing edge therebetween, and the working portion through provision of one or more friction reducing elements is adapted to reduce friction between the instrument and the canal walls to improve the performance of the instrument while reducing the tendency of the instrument to fail under torsional stress.

In one friction reducing embodiment, the point distal from the tissue-removing edge adjacent the periphery, in cross-section, recedes from the periphery at from about an acute angle with respect to a line tangent to the periphery at the point of intersection. The angle is measured from the side of the tangent line distal from the tissue-removing edge.

In another embodiment, the endodontic instrument has at least one outer land, when viewed in cross-section, adjacent the periphery defined by the tissue-removing edge and at least one recessed land. The outer land and the recessed land may be adjacent one another or separated by one or more flutes.

In yet another embodiment, the endodontic instrument comprises at least two flutes spaced apart by a tissue-removing edge or a land which flutes or lands have substantially unequal dimensions when viewed in cross-section. An endodontic instrument may also comprise a combination of two or more of the foregoing preferred embodiments.

These and other features and advantages will be readily apparent to those skilled in the art, having reference to the following detailed description and accompanying drawings, the invention not being limited to any one preferred embodiment.

BRIEF DESCRIPTION OF THE DRAWINGS

FIGS. 4A–C through 16A–C are elevational, longitudinal and cross-sectional views of various preferred embodiments of endodontic instruments having features and advantages as disclosed herein;

DETAILED DESCRIPTION OF THE PREFERRED EMBODIMENT

The figures which will be described hereinbelow illustrate particular preferred embodiments of endodontic instruments having various working portion and cutting tip configurations. The instruments may either be used as reamers/files or condensers/compactors or both, depending on the direction of twist of the helical flutes and lands with respect to the direction of rotation of the instrument.

In all of the embodiments disclosed and described herein, the instruments are represented as reamers or files. However, it will be appreciated that a mirror image of the instrument design may be used as a condenser or compactor for the same direction of rotation of the instrument. Condenser instruments having features as disclosed herein may used to fill void spaces in the root canal cavity.

Figure 1:
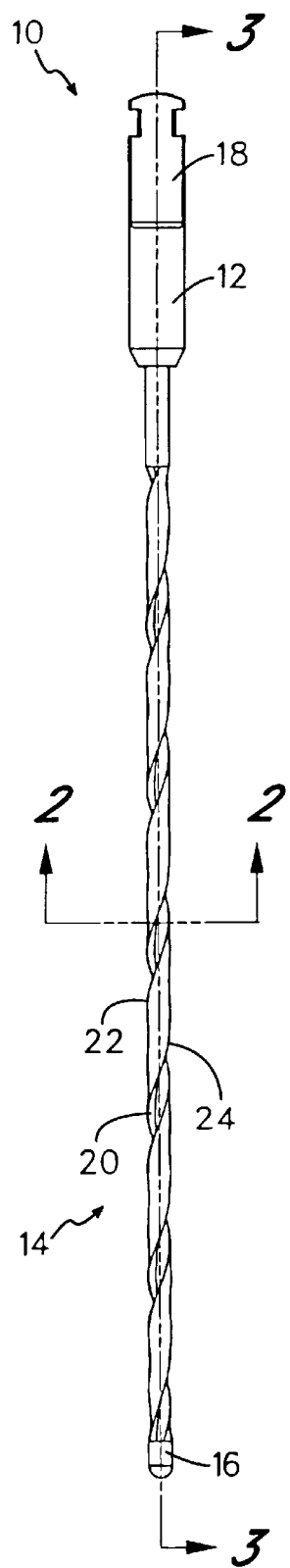
FIG. 1 is an elevational view of a reamer instrument according to one preferred embodiment.

With reference now to FIG. 1, there is illustrated an endodontic instrument according to one preferred embodiment which may be used as a reamer and which has a shaft 10 having a base or proximate end 12 and an elongate working portion 14 extending between the base or proximate end 12 terminating in a tip or distal end 16. The proximate end 12 also contains a fitting portion 18 for mating with a chuck of a dental handpiece (not shown). Alternatively, or in addition to the fitting 18, the proximate end 12 may include a knurled or otherwise treated surface to facilitate hand manipulation of the reamer 10. The working portion 14 of the instrument has a length which may range from about 3 millimeters to about 18 millimeters. A preferred length is about 16 millimeters.

The working portion may have the same cross-sectional diameter between the proximate end 12 and the distal end 16 or the working portion may be tapered in either direction from the proximate end 12 to the distal end 16. When tapered, the taper of the cross-sectional diameter of the working portion 14 may range from about −0.01 to about 0.8 millimeters per millimeter, preferably from about 0.02 to about 0.06 millimeters per millimeter.

The working portion 14 is comprised of one or more helical flutes 20 and one or more helical lands 22 (one each in the embodiment of FIG. 1). In the illustrated embodiment, helical flute 20 and helical land 22 are adjacent tissue-removing edge 24. Helical land 22 and tissue-removing edge 24 are at the periphery of the working portion 14 while flute 20 has a surface 26 (FIGS. 2 and 3) which is recessed from the periphery of the working portion 14 which surface, in cross-section, recedes from the periphery 28 at from about an acute angle 27 with respect to a line 29 tangent to the periphery at the point of intersection B which angle is measured from the side of the tangent line 29 distal from the removing edge 24.

Figure 2:
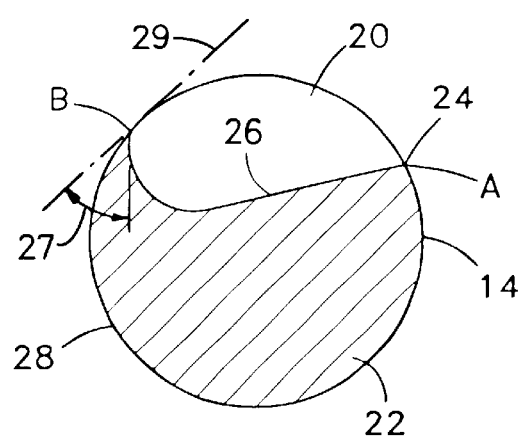
FIG. 2 is a transverse cross-section view of the reamer instrument of FIG. 1 taken along line 2—2 thereof.
Figure 3:
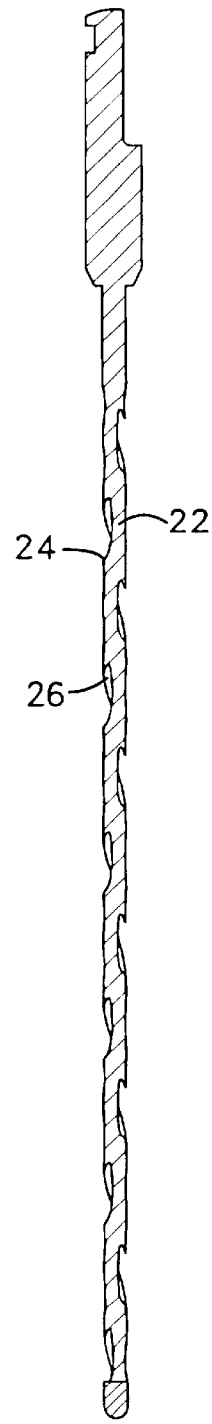
FIG. 3 is a longitudinal view in section of the reamer instrument of FIG. 1 taken along line 3—3 thereof.

As shown in FIGS. 2 and 3, tissue-removing edge 24 is generally opposite a portion of the helical land 22. The wall of flute 20 intersects the periphery of the working portion in the region denoted by the letter A immediately adjacent the periphery 20 of the working portion at an angle of about 90 degrees to tangent to form what is commonly referred to as a zero or neutral rake angle from the perspective of the surface 26 of the flute 20. The rake angle of the tissue-removing edge 24 may be neutral, positive or negative but is preferably about neutral or slightly positive.

It will be appreciated that helical land 22 presents a bearing surface between tissue-removing edge 24 at point A and point B distal from the tissue-removing edge FIG. 2) so that when rotated in a canal, only edge 24 removes tissue while the bearing surface of the helical land 22 bears against the canal wall. In FIG. 2, both point A and point B are located at the periphery 28 of the working portion 14 on generally opposing sides of the land 22.

As illustrated in FIGS. 2 and 3, flute 20 has a concave surface 26 which is recessed from the periphery of the working portion, so that at point B, the surface 26 forms about an acute angle 27 with the line 29 tangent to the periphery. By providing a flute having about an acute angle at B, tissue and debris from the root canal may be more effectively transported and removed from the canal in a direction opposite to the direction of travel of the instrument as the instrument is rotated in the root canal. By removing the debris more effectively from the root canal, there is less friction on the working portion and thus less tendency to shear the instrument by the torque applied to the instrument. The pitch may be constant or may vary, as desired, although a varying pitch is preferred.

For the most effective cutting and tissue removal it is preferred that the pitch of the helical flutes 20 and helical lands 22 range between about 1 spiral per 16 millimeters to about 1 spiral per millimeter along the working portion 14 of the instrument.

Figures 4A, 4B, 4C:
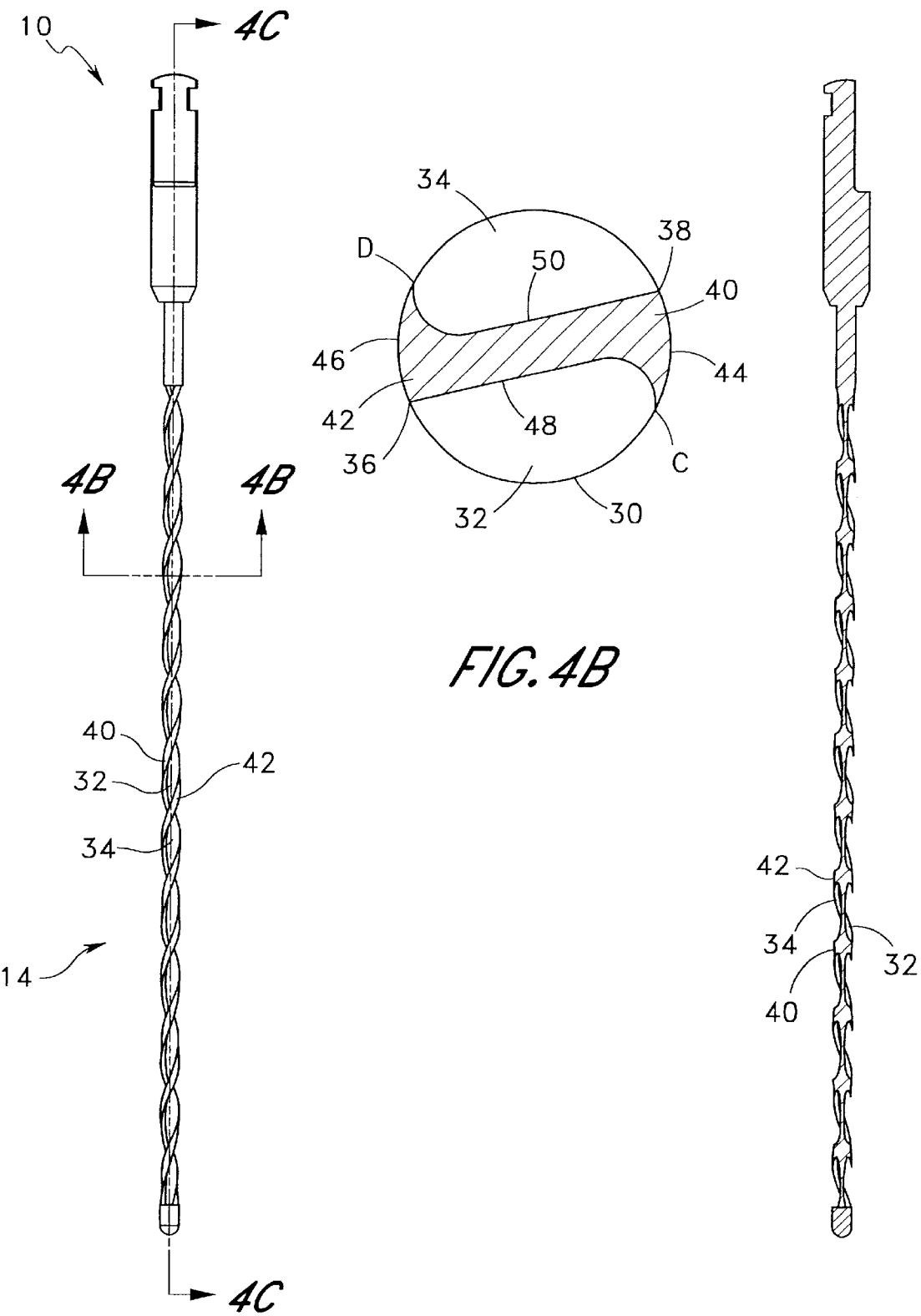

Another endodontic instrument 10 according to the first embodiment illustrated in FIGS. 4A–C wherein FIG. 4A is an elevational view, FIG. 4B is a cross-sectional view along the line 4B—4B of FIG. 4A and FIG. 4C is a partial longitudinal view of FIG. 4A taken along line 4C—4C thereof. The working portion 14 of the instrument illustrated in FIGS. 4A–C contains two helical flutes 32 and 34 and has tissue-removing edges 36 and 38 adjacent two helical lands 40 and 42 which have bearing surfaces 44 and 46. As with the instrument illustrated in FIGS. 1–3, points C and D distal from the tissue-removing edges 36 and 38, respectively, form about acute angles with lines tangent to the periphery at the points of intersection as described above with reference to FIG. 2.

The working portions of endodontic instruments as disclosed herein may be provided with various other friction reducing designs in lieu of or in addition to the above described designs illustrated in FIGS. 1–4C. Such designs may include flutes with receding surfaces as described above, one or more recessed land portions, three or more spaced apart helical lands wherein the spacing between adjacent helical lands in cross-section varies, three or more spaced apart helical tissue-removing edges, various cutting edge designs or a combination of two or more of the foregoing collection means. Cross-sectional configurations of endodontic instruments having alternative designs are illustrated in FIGS. 5A through 16C.

In FIGS. 5A through 6C, the working portion 14 of instrument 10 contains at least one outer helical land 58 adjacent the periphery defined by tissue-removing edge 64 and edge 62 distal from the tissue-removing edge 64 and at least one recessed land 54. As illustrated in FIG. 5B, helical land 52 has a receding wall portion 54 extending from a shoulder 57 to the flute 66 and which is a radial distance $R_1$ from the cross-sectional center 56 of the working portion and a portion 58 which is adjacent the periphery 60 of the working portion which is at a radial distance $R_2$ from the cross-sectional center 56. In this embodiment, helical flutes 66 and 68 are equally spaced apart about helical land 52 and tissue-removing edge 64.

In FIGS. 6A–C, there is again a helical land 70 having at least one outer portion 76 and at least one recessed portion 72. The recessed portion 72 which is at a radial distance $R_1$ from the cross-sectional center 74 of the working portion and a portion 76 of the land 70 is adjacent the periphery 78 of the working portion at a radial distance $R_2$ from the cross-sectional center 74. The periphery 78 is defined by helical tissue-removing edge 82 and point 80 distal from tissue-removing edge 82. In this embodiment, the curvilinear distance between tissue-removing edge 82 and point 80 of helical land 70 is greater than the curvilinear distance between the tissue-removing edge 82 and point 88 of helical land 70.

In the embodiments illustrated in FIGS. 5 and 6, there is a reduction of the force of tissue-removing edges 64 and 82 against the wall of the root canal in the direction perpendicular to the direction of rotation of the instrument in the canal because of the recessed portions 54 and 72 of helical lands 52 and 70. A reduction in force of the tissue-removing edges 64 and 82 with respect to the canal wall provides a reduction in friction during rotation of the instrument in the root canal as the instrument bends to conform to contours of the root canal cavity. The recessed wall portions of the helical lands have a radius $R_1$ which is from about 4 to about 30 percent less than radius $R_2$.

In addition to the recessed wall portions illustrated in FIGS. 5A–C, the instrument illustrated in FIGS. 6A–C also contains tissue-removing edge 82 which is a greater curvilinear distance from point 80 than from point 88 on helical land 70. The unequal curvilinear distances provide unequal cutting forces along the periphery 78 of the working portion of the instrument thereby producing a side-cutting effect which more readily maintains the central axis of a curved root canal.

Figure 7A:
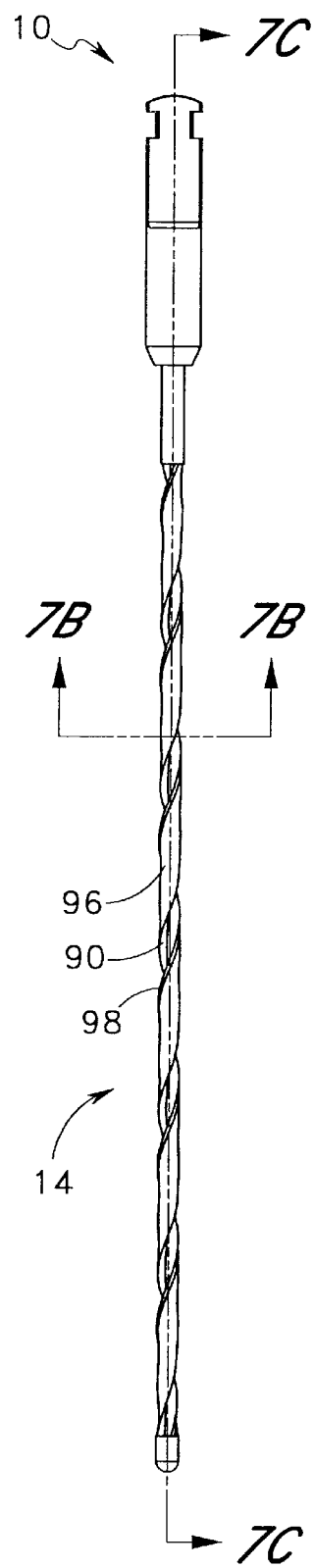

FIGS. 7A through 8C are alternative preferred embodiments of endodontic reamers containing one or more helical flutes which have flute surfaces, in cross-section which recede from the periphery at from about an acute angle with respect to a line tangent to an inside periphery 102 at the point of intersection and one or more helical lands having recessed wall portions. The inside periphery 102 is defined by point E and recessed land portion 106. In FIGS. 7A–C, there is one helical flute 90 having a tissue-removing edge 98 which intersects an outer periphery 92 of the working portion in the region immediately adjacent the outer periphery 92 of the working portion at an angle of about 90 degrees to tangent to form a zero or neutral rake angle from the perspective of the surface 94 of the flute 90.

Helical land 96 provides a bearing surface 106 between point E and tissue-removing edge 98 so that when rotated in a canal, only edge 98 removes tissue while the bearing surface 106 bears against the canal wall. Helical land 96 has an outer land portion 108 adjacent the periphery 92 and a recessed land portion 106 between shoulder F and point E. Recessed land portion 106 has a cross-sectional radius $R_1$ from the cross-sectional center 104 of the working portion and outer land portion 108 has a radius of $R_2$ from the cross-sectional center 104 which is from about 4 to about 30 percent greater than radius $R_1$.

Figure 7B:
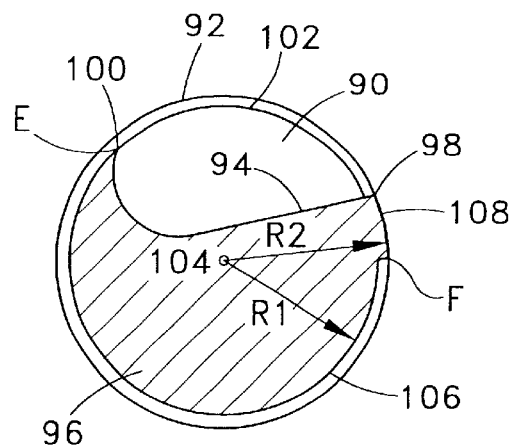
Figure 7C:
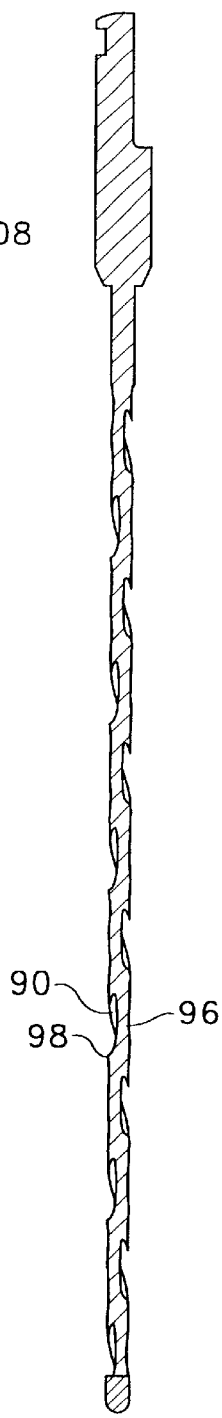

As illustrated in FIG. 7B, the surface 94 of flute 90 which, in cross-section, recedes from the inner periphery 102 at from about an acute angle with respect to a line tangent to the periphery 102 at the point of intersection as illustrated by FIG. 2 above. Flute 90 provides means for collecting and removing tissue or debris from the root canal by transporting the debris opposite to the direction of travel of the instrument as the instrument is rotated in the root canal. In combination with recessed wall portion 106 of helical land 96, the instrument 10 illustrated in FIGS. 7A–C provides reduced friction as the instrument is rotated in the canal due to uneven cutting forces and more effective tissue removal during endodontic procedures.

Figures 8A, 8B, 8C:
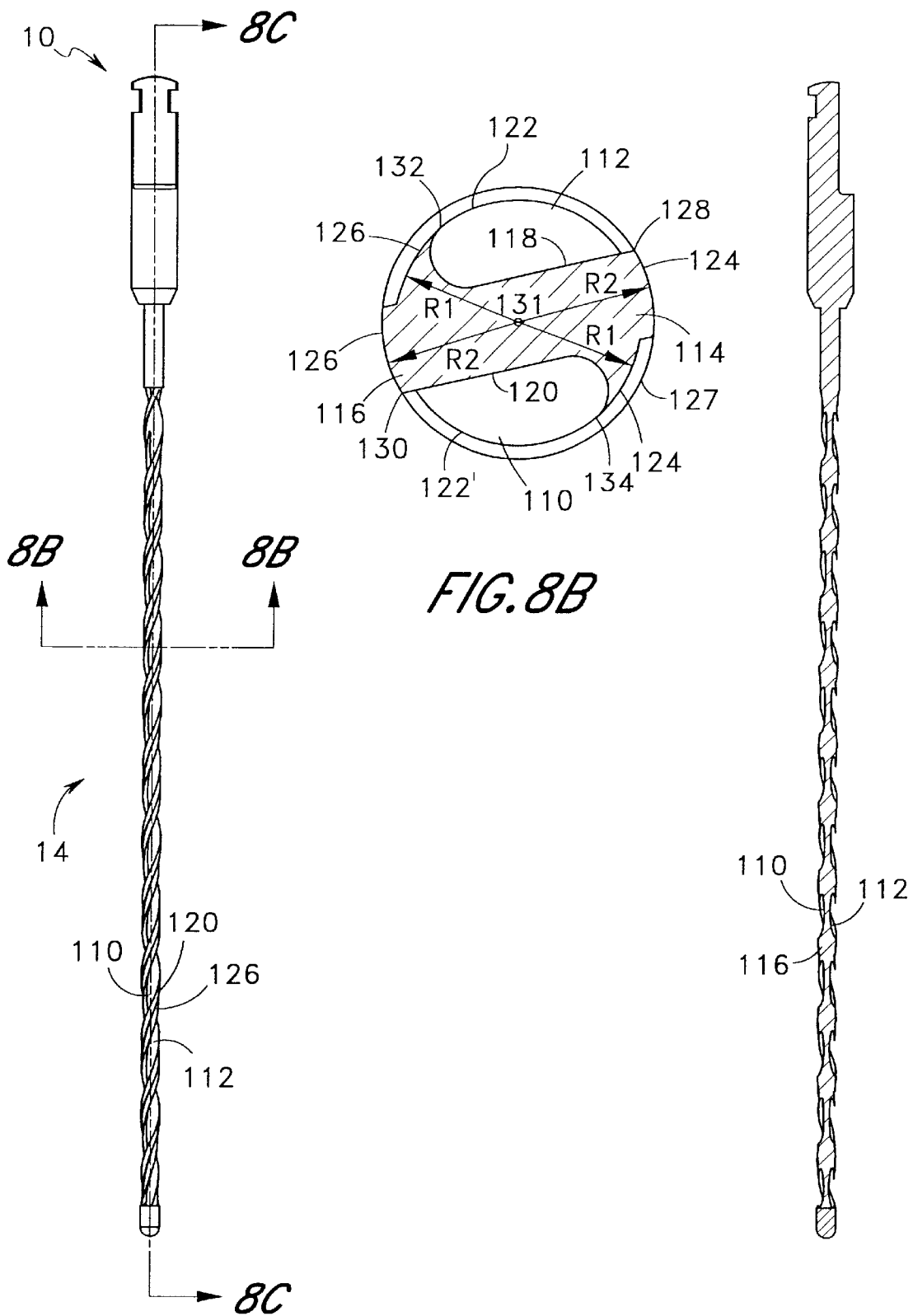

In FIGS. 8A–C, the endodontic instrument contains two helical flutes 110 and 112 and two helical lands 114 and 116. Helical flutes 110 and 112, as illustrated in FIG. 8B, have surfaces 118 and 120 which recede from the inner peripheries 122 and 122' with about acute angles with respect to lines tangent to the peripheries 122 and 122' at the points of intersection 132 and 134 thereof. Outer land portions 124 and 126 of helical lands 114 and I 16 lie on the outer periphery 127 of the working portion of the instrument which is defined by tissue-removing edges 128 and 130, while recessed wall portions 125 and 129 of helical lands 114 and 116 lie at a radial distance $R_1$ from the cross-sectional center 131 which is about 4 to about 30 percent less than radial distance $R_2$ from the center 131 to the periphery 127 of the working portion defined by tissue-removing edges 128 and 130.

FIGS. 9A–C illustrate another embodiment 10 of an endodontic reamer having a working portion 114 containing two diametrically opposed helical flutes 130 and 142 and two diametrically opposed helical lands 144 and 146. In this embodiment, land 146 is an outer land which is adjacent the outer periphery 152 defined by tissue-removing edge 154 and land 144 is recessed land which is adjacent an inner periphery 150 defined by tissue-removing edge 156 as illustrated by FIG. 9B. Recessed land 144 has a radius $R_1$ from the cross-sectional center 148 to recessed land portion on inner periphery 150 and outer land 146 has a radius $R_2$ from the cross-sectional center 148 to outer periphery 152 which is 4 to 30 percent greater than distance $R_1$. An instrument of the design illustrated in FIGS. 9A–C will provide less aggressive tissue removing force with respect to the root canal wall on removing edge 154 as a result of the recessed land portion 146 than the force of removing edge 156. While helical flutes 140 and 142 are illustrated as being equally spaced with respect to removing edges 154 and 156 about the peripheries of the working portion, it will be recognized that unequal spacing of the flutes may also be used.

Figure 10A:
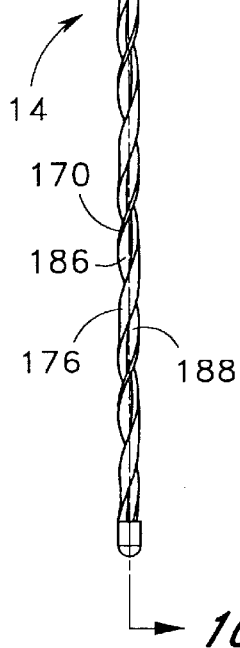
Figure 10B:
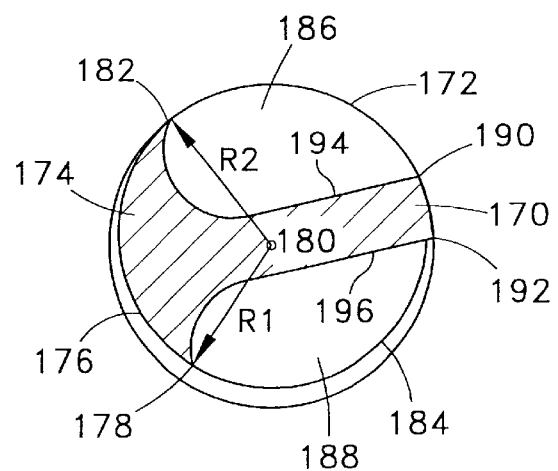
Figure 10C:
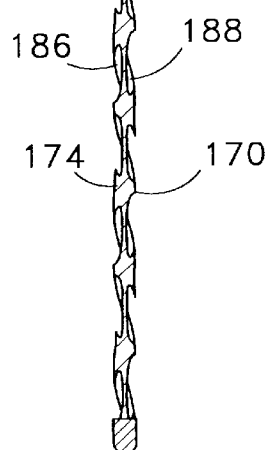

FIGS. 10A–C represent an instrument 10 having a helical land 170 which lies on the periphery 172 of the working portion defined by tissue-removing edge 190 and a helical land 174 having a recessed wall portion 176 which has a radius $R_1$ at point 178 with respect to the cross-sectional center 180 and a wall portion having a radius $R_2$ which lies on the periphery 172. The radius of the wall portion of helical land 174 gradually increases from point 178 which lies adjacent the inner periphery 184 to point 182 which lies adjacent the outer periphery 172 so that helical land 174 has an outer land portion and a recessed land portion as illustrated in FIG. 10B. The recessed portion 176 of land 175 provides a reduction in the cutting force of cutting edge 190 and therefore reduces the friction with respect to the root canal walls during rotation of the instrument.

Spaced apart helical flutes 186 and 188 of the instrument illustrated in FIGS. 10A–C each have surfaces 194 and 196, in cross section, which recede at about acute angles to lines tangent to the peripheries 172 and 184 at the points 182 and 178 respectively. FIGS. 10A–C therefore represent an endodontic instrument 10 containing a combination of a recessed land and the helical flutes described in FIGS. 1–3 which reduces friction and/or has better removal efficiency of material from the root canal during an endodontic procedure.

Figures 11A, 11B, 11C:
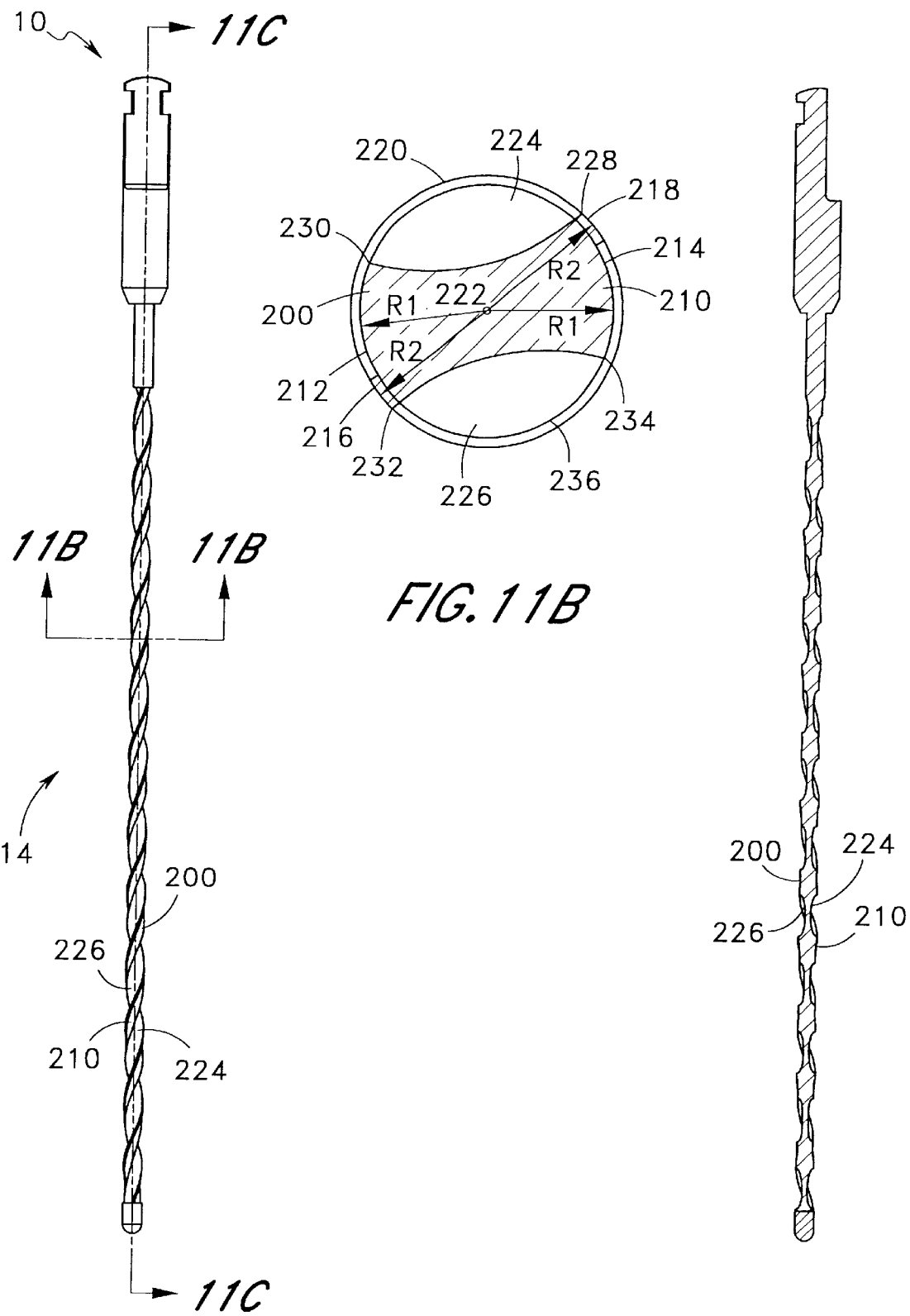

FIGS. 11A–C provide a variation of an endodontic instrument as described above which combines the features illustrated and described by reference to FIGS. 9A–C above with recessed land portions. In FIG. 11B there are two opposing helical lands 200 and 210 separated by helical flutes 224 and 226. Helical land 200 has a recessed wall portion 212 and an outer wall portion 216, and helical land 210 has a recessed wall portion 214 and an outer wall portion 218. The recessed wall portions 212 and 214 lie on an inner periphery 236 defined by points 230 and 234 which are distal to tissue-removing edges 228 and 232. The recessed portions 212 and 214 are at a radial distance of $R_1$ in cross section from the cross-sectional center 222 of the working portion, and outer land portions 216 and 218 lie at a radial distance $R_2$ from the center 222 and adjacent an outer periphery 220 of the working portion defined by tissue-removing edges 228 and 232. Radius $R_2$ is at a distance which is 4 to 30 percent greater than $R_1$ with respect to the center 222. Helical flutes 224 and 226 are disposed about the periphery of the working portion so that the curvilinear distance between tissue-removing edge 228 and point 230 is substantially the same as the curvilinear distance between tissue-removing edge 232 and point 234. However, unequal curvilinear flute distances may also be used for increased cutting efficiency as described above with respect to FIGS. 6A–C.

FIGS. 12A–C illustrate a reamer or file having a combination of the features illustrated by FIGS. 1–3 with unequally spaced flutes 240 and 242 illustrated by FIGS. 6A–C and unequally sized opposing lands 244 and 246. According to this embodiment, the working portion 14 contains at least one helical flute 240, wherein point 252 distal from tissue-removing edge 250, in cross section, recedes at about an acute angle with respect to a line tangent to the periphery 248 at the point of intersection, as shown in FIG. 12B and described with reference to FIGS. 1–3 above. As illustrated in FIG. 12B, the curvilinear distance from tissue-removing edge 254 to point 252 is greater than the curvilinear distance from tissue-removing edge 250 to point 256. Hence, the bearing surface 258 of helical land 246 is substantially greater than the bearing surface 260 of helical land 244. The unequal bearing surfaces of the lands provide unequal tissue removal efficiencies along the periphery 248 of the working portion of the instrument, thereby producing a side-cutting effect which more readily maintains the central axis of a curved root canal.

Figures 13A, 13B, 13C:
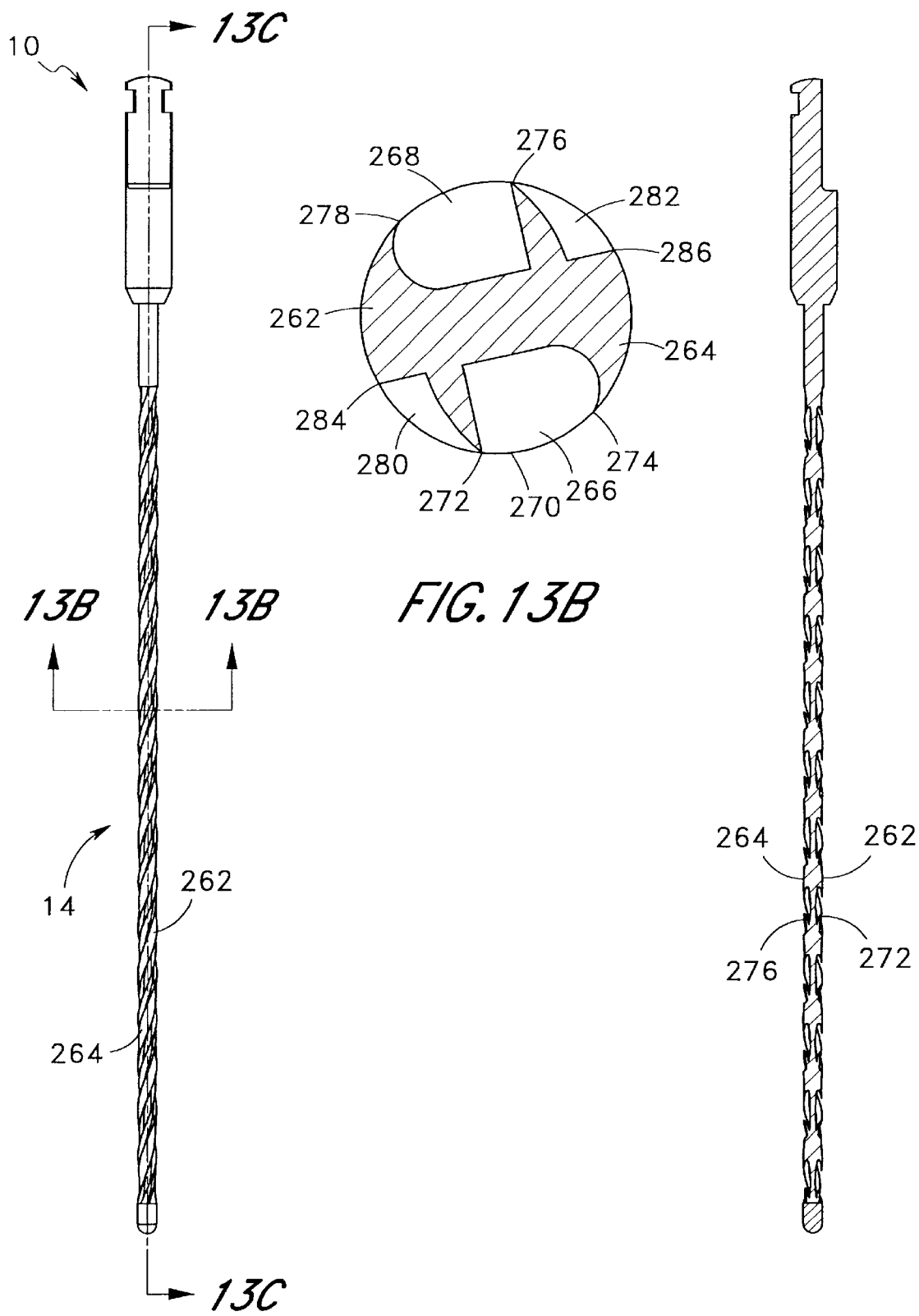

A combination of two of the before-mentioned proffered embodiments is illustrated in FIGS. 13A–C. With reference to FIG. 13B, the endodontic instrument 10 contains two helical lands 262 and 264 and two helical flutes 266 and 268. Helical flute 266 is between tissue-removing edge 272 and point 274 distal to removing edge 272, and helical flute 268 is between tissue-removing edge 276 and point 278 distal to removing edge 276. Points 274 and 278 recede at from about acute angles with respect to a line tangent to the periphery 270 at the points of intersection therewith, as described by reference to FIG. 2 above. The curvilinear distances along the periphery 270 of the working portion from tissue-removing edge 272 to point 274 may be substantially the same as the curvilinear distance from removing edge 276 to point 278, as illustrated, or the distances may be unequal.

In the illustrated embodiment of FIGS. 13A–C, there are also provided two helical flutes 280 and 282 between tissue-removing edges 284 and 272 and between tissue-removing edges 286 and 276 which are substantially smaller in volume than flutes 266 and 268. Again, the curvilinear distance between tissue-removing edges 272 and 284 may be substantially the same as the curvilinear distance between tissue-removing edges 286 and 276, or the distances may be unequal, as desired.

Figures 14A, 14B, 14C:
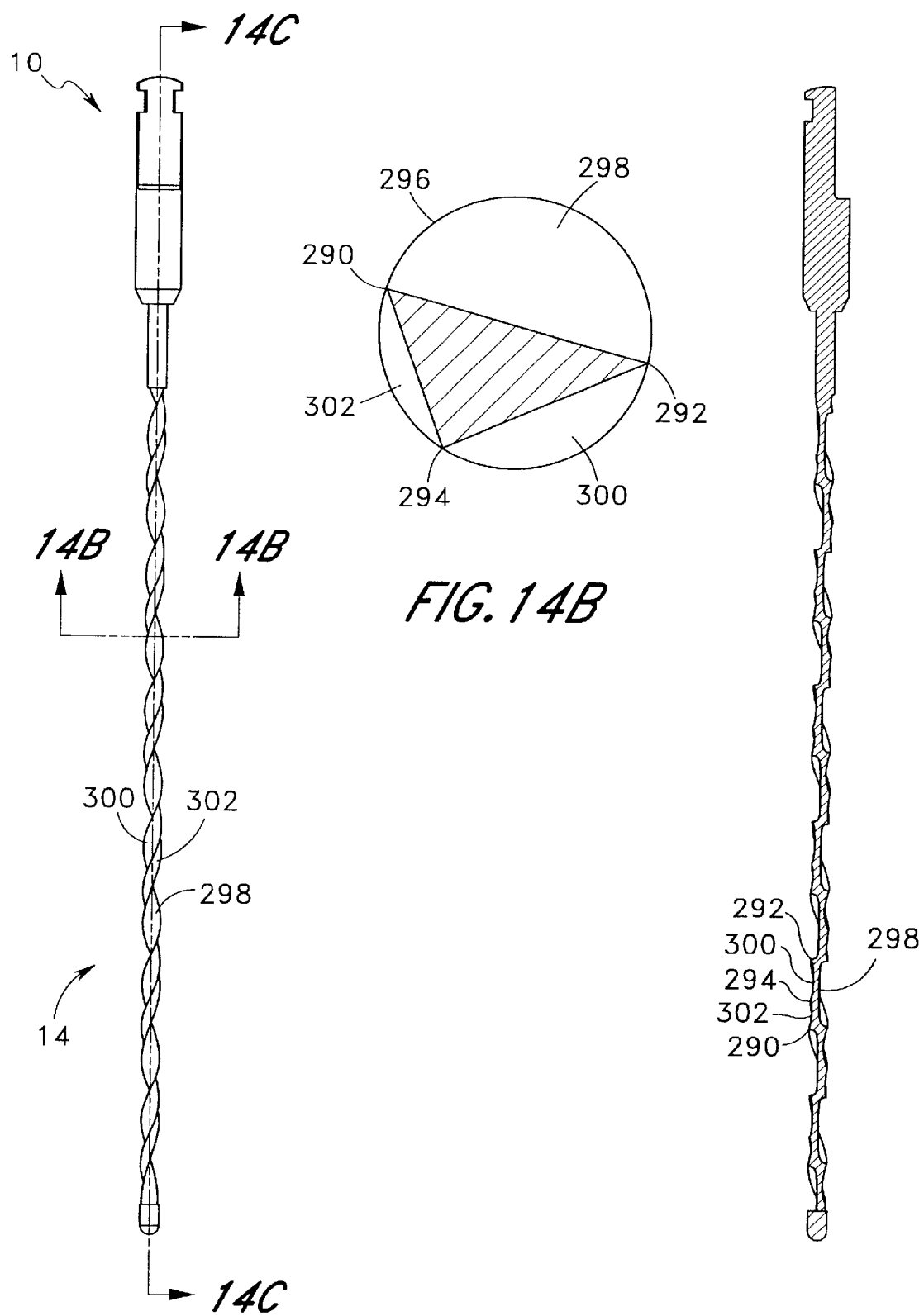

The endodontic instrument 10 illustrated in FIGS. 14A–C contains three spaced-apart tissue-removing edges 290, 292, and 294 defining the working portion periphery 296. Helical flute 298 lies between tissue-removing edges 290 and 292, helical flute 300 lies between tissue-removing edges 292 and 294, and helical flute 302 lies between tissue-removing edges 294 and 290 such that the curvilinear distance along the periphery 296 from removing edge 290 to removing edge 292 is greater than the curvilinear distance from removing edge 292 to removing edge 294, which in turn is greater than the curvilinear distance from removing edge 294 to removing edge 290. In the alternative, the curvilinear distances between removing edges 292 and 294 and removing edges 294 and 290 may be substantially the same. In another alternative embodiment, flutes 298, 300, and 302 may be all of substantially equal volume.

Figures 15A, 15B, 15C:
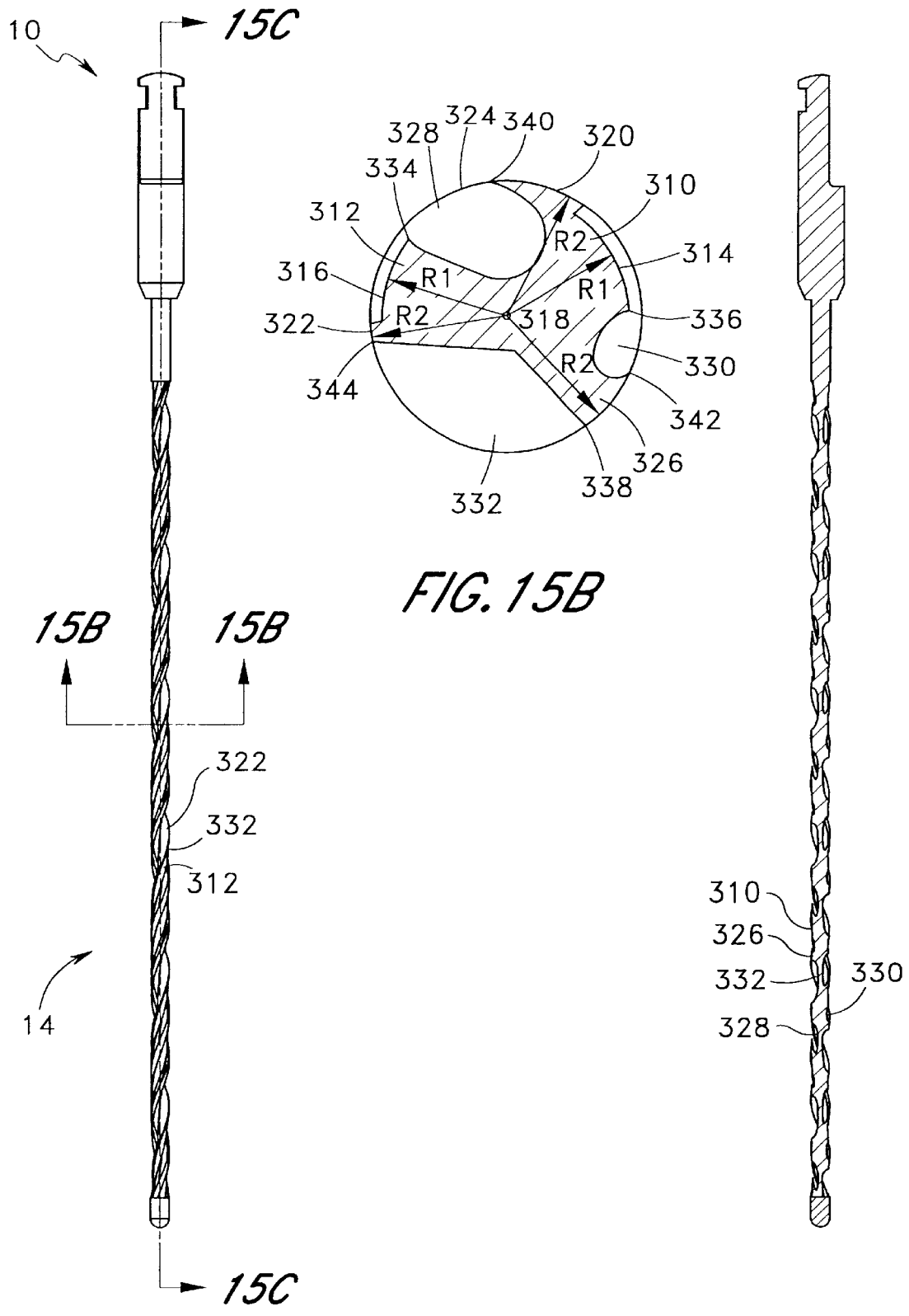

FIGS. 15A–C represent yet another embodiment of an endodontic instrument 10 having features disclosed herein, including a combination of helical flute designs and one or more recessed helical land portions. In FIGS. 15A–C there are two helical lands 310 and 312, each having outer land portions 320 and 322 adjacent the periphery 324 defined by tissue-removing edge 338 and recessed land portions 314 and 316 which lie at a radial distance $R_1$ from the cross-sectional center 318 of the working portion 14, as illustrated in FIG. 15B. Helical land portions 320 and 322 and helical land 326 all lie adjacent the periphery 324 of the working portion at a distance $R_2$ from the cross-sectional center 318. In this embodiment, helical land 326 does not contain a recessed land portion; however, all three lands 310, 312, and 326 may contain recessed land portions.

In the instrument illustrated by FIG. 15B, there are three helical flutes 328, 330, and 332. Helical flute 328 lies between tissue-removing edge 334 and point 340 distal to removing edge 334, helical flute 330 lies between tissue-removing edge 336 and point 342 distal to removing edge 336, and helical flute 332 lies between tissue-removing edge 338 and point 344 distal to removing edge 338. As described above with reference to FIG. 2, points 340 and 342 recede at from about an acute angle with respect to lines tangent to the periphery 324 at the point of intersection thereof. Furthermore, the curvilinear distance from tissue-removing edge 338 to point 344 is greater than the curvilinear distance from tissue-removing edge 334 to point 340, which in turn is greater than the curvilinear distance between tissue-removing edge 336 and point 342. Accordingly, this embodiment combines the recessed land features with the flutes of FIGS. 1–3 and the unequal spacing between adjacent flutes of FIGS. 6A–C.

FIGS. 16A–C provide another design of an endodontic instrument 10 having features as disclosed herein. In this design there are three helical flutes 350, 352, and 354 in the working portion 14 and three spaced-apart helical lands 356, 368, and 360. The curvilinear distance along the periphery 362 of the working portion from tissue-removing edge 366 to point 364 distal to removing edge 366 is substantially greater than the curvilinear distance from tissue-removing edge 370 to point 368, as shown in FIG. 16B. Likewise, the curvilinear distance along the periphery 362 from tissue-removing edge 374 to point 372 is greater than the curvilinear distance from removing edge 370 to point 368 and may be substantially the same, greater than, or less than the curvilinear distance from tissue-removing edge 366 to point 364. In this embodiment the surfaces 376, 378, and 380 of flutes 350, 352, and 354 are angular rather than rounded when viewed in cross section (FIG. 16B).

As described above with reference to FIG. 2, the points 364, 368, and 372 distal from removal edges 366, 370, and 374, respectively, recede at about acute angles with respect to a line tangent to the periphery at the points of intersection therewith. Accordingly, the instrument illustrated by FIGS. 16A–C provides tissue-removal efficiencies along the periphery 362 of the working portion, which are enhanced by producing a side-cutting effect which more readily maintains the central axis of a curved root canal.

The endodontic instruments described above provide reduced resistance during endodontic procedures and/or improved removal of material from the root canal of a tooth because of their design. These endodontic instruments are also believed to possess improved side-cutting capability and an inherent propensity to work into canal areas that are non-circular so as to remove material from nooks previously untouched or insufficiently worked by conventional instruments, as well as to reduce the propensity for the instruments to break during endodontic treatment procedures.

For additional strength it is preferred that the diameter of the web, or uncut core portion of the endodontic instruments described above, be from about 10 to about 80 percent of the cross-sectional diameter of the working portion. Web diameters greater than about 80 percent may make the instruments too rigid to bend around the curved portions of the root canal, while core diameters of less than about 10 percent may not be rigid enough to provide effective cutting or compacting of material in the root canal.

Another preferred embodiment of an endodontic file having features and advantages as disclosed herein is shown and illustrated in FIGS. 17A–E. In this particular embodiment the endodontic file includes two opposing helical lands 400 and 410 separated by helical flutes 424 and 426, as illustrated in the sectional view shown in FIG. 17D. Helical land 400 has a recessed wall portion 412 and an outer wall portion 416, and helical land 410 has a recessed wall portion 414 and an outer wall portion 418. The recessed wall portions 412 and 414 lie on an inner periphery defined by points 430 and 434 which are distal to tissue-removing edges 428 and 432. The recessed portions 412 and 414 are at a first predetermined radial distance from the cross-sectional center of the working portion 14, and outer land portions 416 and 418 lie at a second predetermined radial distance from the center of the working portion 14. The outer periphery 420 of the working portion 14 includes tissue-removing edges 428 and 432. Helical flutes 424 and 426 are disposed about the periphery of the working portion so that the curvilinear distance between tissue-removing edge 428 and point 430 is different from the curvilinear distance between tissue-removing edge 432 and point 434. The lands 416, 418 are also preferably unevenly spaced around the periphery of the working portion 14, as represented by the offset or "clocking" angle a in FIG. 17C. Table 1, below, provides preferred dimensions and specifications for one possible embodiment of an endodontic file having features and advantages as disclosed herein:

TABLE 1

|  | NOMINAL | PLUS | MINUS |
| --- | --- | --- | --- |
| DIAMETER AT TIP | 0.0098 | 0.0004 | 0.0004 |
| DIAMETER TAPER RATE | 0.050 |  |  |
| SHANK DIAMETER | 0.0413 | 0.0003 | 0.0003 |
| FLUTE LENGTH | 0.6300 | 0.0100 | 0.0100 |
| RELIEF LENGTH | 0.6300 | 0.0100 | 0.0100 |
| HELIX @ POINT A | 30° | 1° | 1° |
| HELIX @ POINT B | 45° | 1° | 1° |
| WEB THICKNESS @ POINT A | 0.0029 | 0.0006 | 0.0006 |
| LAND WIDTH @ POINT A | 0.0053 | 0.0004 | 0.0004 |
| LAND WIDTH @ POINT B | 0.0275 | 0.0004 | 0.0004 |
| RELIEF DIAMETER @ POINT | 0.0078 | 0.0008 | 0.0008 |
| MARGIN WIDTH @ POINT A | 0.0019 | 0.0004 | 0.0004 |
| MARGIN WIDTH @ POINT B | 0.0128 | 0.0004 | 0.0004 |
| WEB TAPER RATE | 0.0300 | 0.0040 | 0.0040 |
| POINT ANGLE | 90° | 2° | 2° |
| PRIMARY ANGLE | 15° | 1° | 1° |
| FLUTE CLOCKING ANGLE | 175° | 1° | 1° |
| OVERALL LENGTH | 1.2000 | 0.0010 | 0.0010 |

REFERENCE DIMENSIONS ONLY
RAKE ANGLE RATE @ POINT 14°
RAKE ANGLE @ POINT A -10°
RAKE ANGLE RATE @ POINT -34°
RAKE ANGLE RATE @ POINT -35°

Figure 17A:
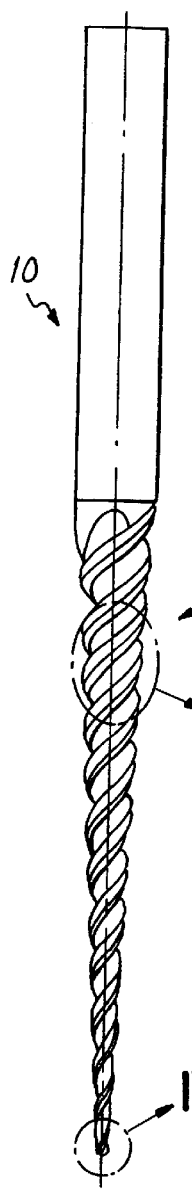
FIG. 17A is an elevational view of a reamer instrument including a chisel tip.
Figure 17E:
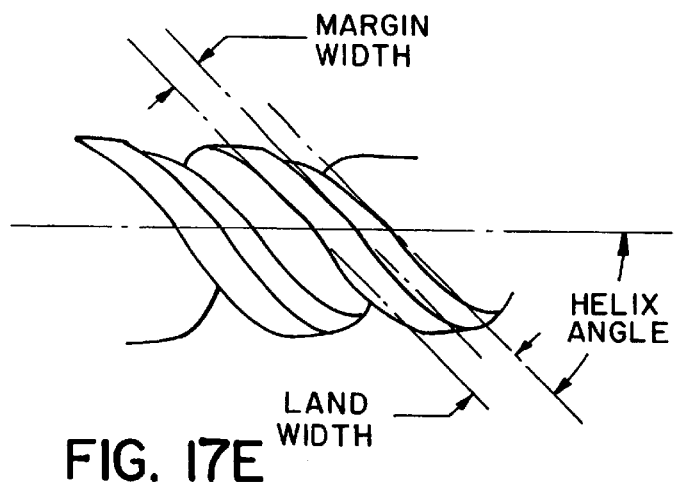
FIG. 17E is a side elevational detail view of the encircled area 17E of the reamer instrument shown in FIG. 17A.
Figure 17B:
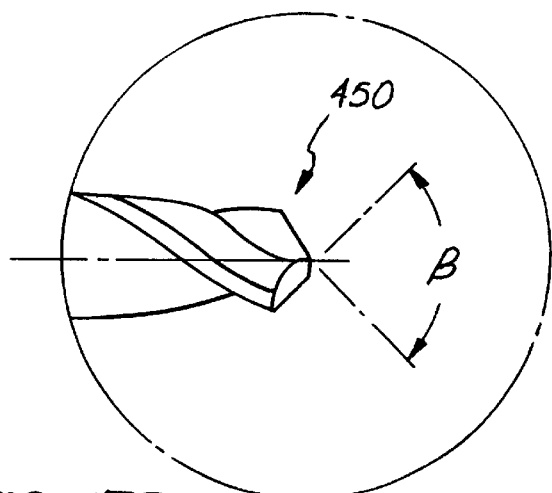
FIG. 17B is an enlarged side elevational detailed view of encircled area 17B of FIG. 17A.
Figure 17C:
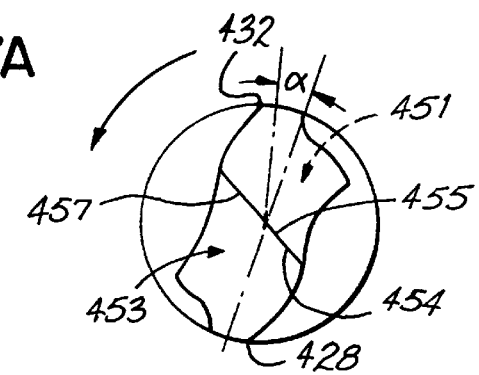
FIG. 17C is a detailed end view of the chisel tip of the reamer of FIG. 17A.
Figure 17D:
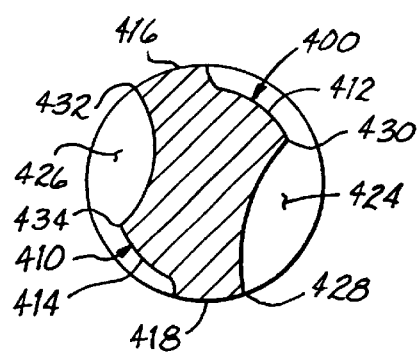
FIG. 17D is a transverse cross-section view of the reamer of FIG. 17A through a point adjacent the chisel tip portion.

An important feature of the file 14 as shown in FIGS. 17A–E is the chisel tip portion 450, shown in more detail in FIGS. 17B and 17C. The chisel tip portion 450 generally comprises two or more facets 451, 453 which intersect along a substantially linear chisel edge 454 that is substantially orthogonal to a longitudinal axis of the elongate working portion 14. Upon rotation of the tip portion 450 in the root canal, each of the facets 451, 453 scrapes or removes tissue along respective chisel edges 455, 457 that are substantially collinear with each other along the chisel edge 454. Preferably, the facets 451, 453 and the intersecting tissue removing edges 432, 428 are unequally spaced about the periphery of the working portion as represented by the offset or "clocking " angle α in FIG. 17C.

Figure 18:
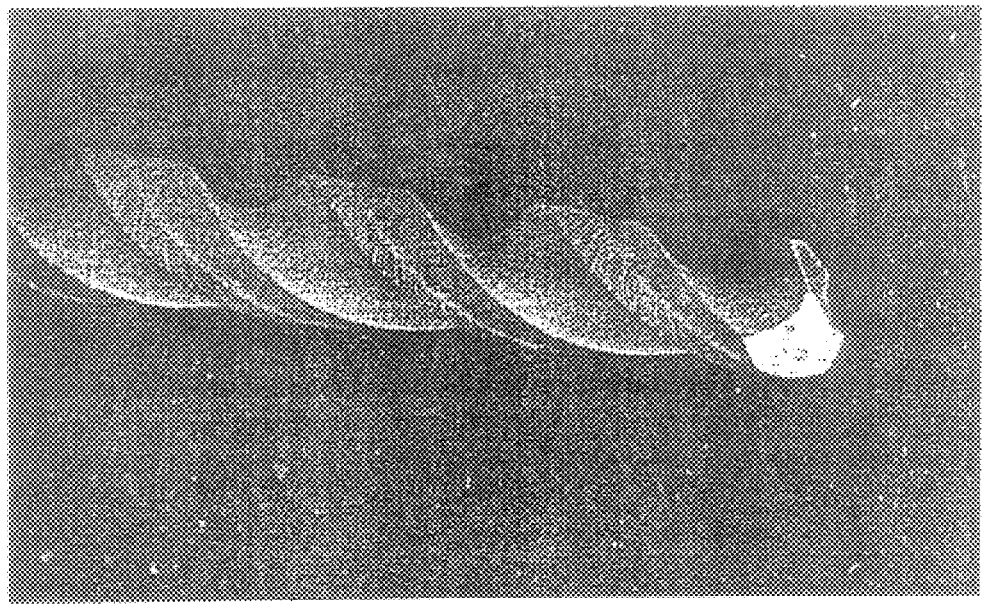
FIG. 18 is an SEM photograph (magnification 25×) of a chisel tip portion of an endodontic file having features as disclosed herein.
Figure 19:
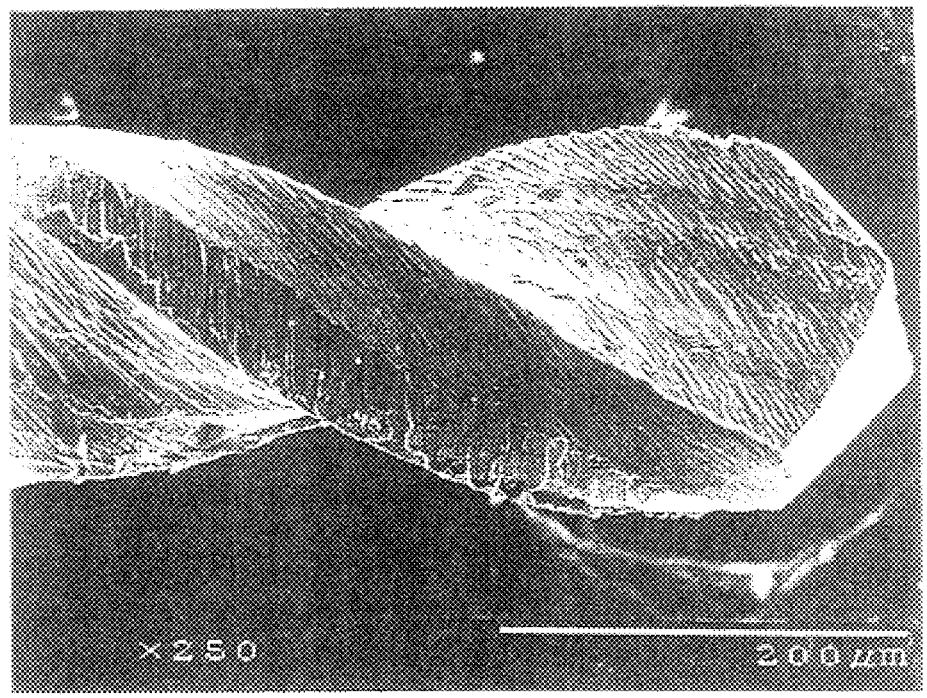
FIG. 19 is an SEM photograph (magnification 250×) of a chisel tip portion of an endodontic file having features as disclosed herein.

The chisel tip may be formed by grinding flats or facets 451, 453 into the tip of the tool, as shown, forming a chisel edge 455. The facets 451, 453 may be formed having an included tip angle β of between about 60 degrees and 100 degrees, and more preferably about 90 degrees. The chisel edge 455 is preferably canted from center by a primary angle of about 5 to 25 degrees and more preferably about 15 degrees, as shown in FIG. 17C. The particular geometry of the chisel tip 450 is shown in more detail in FIGS. 18 and 19. FIG. 18 is an SEM photograph of the tip portion of an endodontic file having the above-described features viewed at a magnification of 25×. FIG. 19 is an SEM photograph of the tip portion of an endodontic file having the above-described features viewed at a magnification of 250×. While a two-facet chisel tip is shown, those skilled in the art will readily appreciate that any one of a number of multifaceted chisel tip designs may be used while enjoying the benefits and advantages as disclosed herein. For example, a four-faceted chisel tip may provide a suitable compromise for many endodontic applications.

Figure 20:
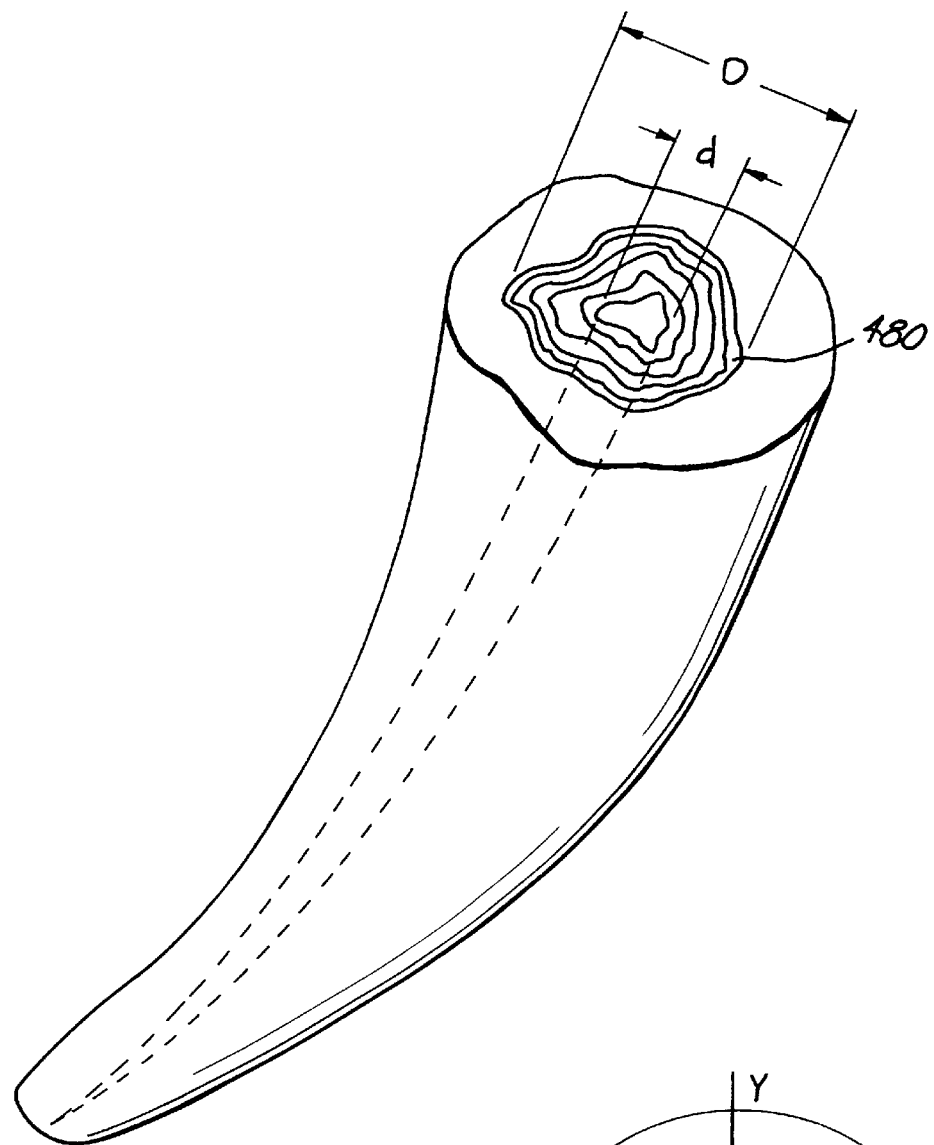
FIG. 20 is a representational partial schematic drawing of a typical calcified root canal.

As will be explained in more detail below, the particular tip geometry disclosed and described herein reduces the cutting friction between the instrument, and the tooth canal, improves cutting efficiency and performance of the instrument, while reducing the tendency of the instrument to fail under torsional stress. It will be recalled from the earlier discussions that most conventional endodontic files rely on a blunt or rounded tip in order to prevent transportation of the file through the root canal wall. While this design has fair success when used to extirpate and enlarge a root canal having a relatively large canal opening (ie. large enough to accommodate insertion of the blunt tip), a problem is often encountered with root canals, particularly in older patients, which have become built-up with calcium accretion 480, as shown in FIG. 20. In that case, the root canal opening which would normally be of diameter "D" is constricted to a smaller diameter "d".

For these small root canal openings it is difficult to enter the canal with a conventional file having a blunt or rounded tip because the instrument at that point has little or no cutting or abrading ability. Rather, the instrument must grind or burnish its way into the canal before any cutting action takes place and even then the cutting action only occurs at the periphery of the instrument and not at the tip. This increases the wear and tear on the instrument, increases the risk of breakage and, in addition, can cause heating in the canal which can damage surrounding tissue. Moreover, there is a practical limit to how small the tip can be on an endodontic file without compromising the integrity of the instrument which could lead to failure in the canal. Conventional files have tip diameters that are as small as 0.06 mm. But even these small instruments have difficulty penetrating into root canals where significant calcium accretion has occurred.

Heretofore, it was widely believed that the use of a cutting point having sharp edges was undesirable because it would lead to transportation through the root canal wall. It has been discovered however, that at least some cutting ability on the tip is desirable, particularly if the tip has the preferred geometries as shown. In particular, the chisel tip 450 as shown and described in connection with FIGS. 17–19 provides cutting ability at the tip of the instrument (albeit at a significantly negative rake) which dramatically improves the ability of the instrument to penetrate the small opening of a calcified root canal. This not only reduces the heat and friction generated during the procedure, but also speeds up the procedure, reduces wear and tear on the instrument, and the risk of instrument breakage in the canal.

In a particularly preferred embodiment of an endodontic file having a chisel tip 450, as shown in FIG. 17C, the facets 451, 453 and intersecting removing edges 428, 432 are spaced unevenly about the periphery of the working portion as represented by the clocking angle α. This unequal spacing provides not only the benefits of more even side cutting, as described above, but it also produces desirable asymmetries in the chisel tip portion 450 of the file which give the tip 450 a tendency to "wander" or "wobble" as the instrument is rotated, as described in more detail below in connection with FIG. 21. This is particularly advantageous for extirpating a curved or convoluted root canal because the tip tends to probe around and follow the path of least resistance down the root canal, rather than make a straight path through the canal wall. The wandering tip combined with the ability to cut or abrade the material more efficiently produces an endodontic file that is faster and more efficient at cutting, while still avoiding undesirable risks of penetrating the root canal wall.

Figure 21:
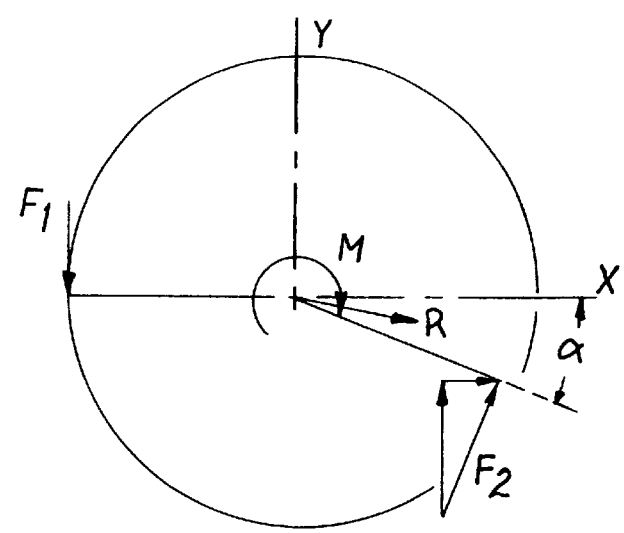
FIG. 21 is a schematic free body diagram illustrating the effects of asymmetric forces exerted on the chisel tip portion of an endodontic instrument having features as disclosed herein.

FIG. 21 is a schematic free body diagram illustrating the effects of asymmetric forces exerted on the chisel tip portion of an endodontic instrument having features as disclosed herein. In operation, the tip is subjected to a rotational driving force represented as the moment "M". This moment produces certain reaction forces at the tip of the instrument represented as forces $F_1$ and $F_2$. Those skilled in the art will appreciate that the forces $F_1$ and $F_2$ are schematic representations of the actual forces exerted on the tip of the file which are distributed throughout the facets and edges comprising the tip. The simplified schematic representation of these forces, however, is useful to illustrate the wandering dynamics of the chisel tip portion of an endodontic file having features as disclosed herein.

Assuming mean equilibrium conditions at the tip, the moment created by forces $F_1$ and $F_2$ acting about the rotational centerline of the file will counterbalance the moment "M" such that the two moments cancel out and the rotational speed of the tip is constant. On the other hand, due to the aforementioned asymmetries in the tip geometry, the forces $F_1$ and $F_2$, although equal in mean absolute magnitude, will not cancel out. This is because the force $F_2$ has a negative Y component that is equal to the magnitude of the force $F_1$, while the force $F_2$ has both positive X and Y components that are equal to the magnitude of the force $F_2$ multiplied by the sine and cosine of the clocking angle $\alpha$, respectively. Thus, assuming the magnitudes of the forces $F_1$ and $F_2$ are equal, the net resultant force R on the tip will have an X component equal to $F_2 \cdot (\sine \alpha)$ and a Y component equal to $-F_2 \cdot (1-\cos \alpha)$. Of course, the magnitude and direction of the resultant force R will change with the rotation of the instrument in the root canal, thus achieving the desired wandering effect described above. Alternatively, tip asymmetries can also be achieved in other ways, as will readily appreciated by those skilled in the art, such by making the rake angles of the removing edges 428, 432 (FIG. 17C) different from one another and/or by recessing one of the removing edges.

The endodontic instruments described herein may be used by manipulating the instrument manually in a rotating action, or the instrument may be manipulated by attaching the proximate end (FIG. 1) of the instrument to a motorized device for effecting the removal of material in the root canal.

The rake angles of the tissue-removing edges may be positive, negative, or neutral, but are preferably about neutral or slightly positive with respect to the periphery of the working portion. Alternatively, the rake angles of one or more tissue-removing edges may be different from one another such that one may be substantially positive and another may be substantially neutral or negative. The rake angle of one or more removal edges may also vary along the length of the working portion, as desired, or as may be convenient for purposes of manufacturing the instruments. In order to make the instruments having the desired rake angles and configurations, the instruments may be ground from a straight or tapered rod, twisted, and/or drawn to a taper with or without grinding.

The endodontic instruments in accordance with the preferred embodiments described above are preferably made from a strong, highly elastic material such as nickel-titanium, Nitinol™ or other suitable alloy. They can also be made from surgical stainless steel, if desired. A particularly preferred material is titanium 13—13 or a nickel-titanium alloy comprising about 56% nickel and about 44% titanium, such as SE508 nickel-titanium wire available from Nitinol Devices and Components, inc. of Freemont Calif. Those of ordinary skill will recognize that any one of a variety of well known techniques for making conventional instruments may generally be applied to the manufacture of instruments as disclosed herein with various known or later developed improvements in materials or processing. Suitable grinding techniques which may be used are described in standard metallurgical texts for grinding various metals. Good results have also been reported using a relatively fine grit-grinding surface rotating at a relatively slow speed to form the necessary tissue removing edges and lands.

This invention has been disclosed and described in the context of various preferred embodiments. It will be understood by those skilled in the art that the present invention extends beyond the specific disclosed embodiments to other alternative possible embodiments, as will be readily apparent to those skilled in the art. Thus, it is intended that the scope of the present invention herein disclosed should not be limited by the disclosure herein, except as encompassed by a fair reading of the claims which follow.

What is claimed is:

1. An endodontic dental instrument for extirpating and enlarging a root canal, comprising:

an elongate working portion having a length of from about 3 to about 18 millimeters, a peripheral diameter ranging from about 0.08 millimeters to about 1.9 millimeters, at least one helical flute, at least one tissue-removing edge, and at least one outer helical land portion, the helical flute and helical land portion each having a pitch ranging from about 1 spiral per 16 millimeters to about 1 spiral per millimeter; and a chisel tip at an end of said working portion, said chisel tip portion comprising a plurality of facets which intersect along a chisel edge, said facets intersecting said working portion at respective tissue-removing edges disposed at the periphery of said working portion, said tissue-removing edges being unequally spaced about said periphery.

* * * * *

UNITED STATES PATENT AND TRADEMARK OFFICE
CERTIFICATE OF CORRECTION

PATENT NO.    : 6,419,488 B1
DATED         : July 16, 2002
INVENTOR(S)   : John T. McSpadden et al.

It is certified that error appears in the above-identified patent and that said Letters Patent is hereby corrected as shown below:

Column 7,
Line 36, reads "lands 114 and I 16 lie" and should read -- lands 114 and 116 lie --.

Column 11,
Line 11, reads "angle a in FIG. 17C" and should read -- angle α in FIG. 17C --.

Column 12,
Line 8, reads "between the instrument, and the tooth canal, improves" and should read -- between the instrument and the tooth canal, improves --.

Column 13,
Line 2, reads "This is because the force $F_2$ has a negative" and should read -- This is because the force $F_1$ has a negative --.

Signed and Sealed this

Eighteenth Day of March, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,419,488 B1
DATED         : July 16, 2002
INVENTOR(S)   : John T. McSpadden et al.

It is certified that error appears in the above-identified patent and that said Letters Patent is hereby corrected as shown below:

Column 7,
Line 36, reads "lands 114 and I 16 lie" and should read -- lands 114 and 116 lie --.

Column 11,
Line 11, reads "angle a in FIG. 17C" and should read -- angle α in FIG. 17C --.

Column 12,
Line 8, reads "between the instrument, and the tooth canal, improves" and should read -- between the instrument and the tooth canal, improves --.

Column 13,
Line 26, reads "This is because the force $F_2$ has a negative" and should read -- This is because the force $F_1$ has a negative --.

This certificate supersedes Certificate of Correction issued Mach 18, 2003.

Signed and Sealed this

Fifteenth Day of July, 2003

JAMES E. ROGAN
*Director of the United States Patent and Trademark Office*